(12) United States Patent
Ishida et al.

(10) Patent No.: US 12,280,127 B2
(45) Date of Patent: *Apr. 22, 2025

(54) COMPOSITION FOR FORMING COATING FILM

(71) Applicant: KAO CORPORATION, Tokyo (JP)

(72) Inventors: Kaori Ishida, Utsunomiya (JP); Shingo Hirono, Cincinnati, OH (US); Tatsuya Fujimoto, Sumida-ku (JP); Hideo Kobayashi, Moka (JP)

(73) Assignee: KAO CORPORATION, Tokyo (JP)

( * ) Notice: Subject to any disclaimer, the term of this patent is extended or adjusted under 35 U.S.C. 154(b) by 740 days.

This patent is subject to a terminal disclaimer.

(21) Appl. No.: 17/614,774

(22) PCT Filed: May 29, 2020

(86) PCT No.: PCT/JP2020/021416
§ 371 (c)(1),
(2) Date: Nov. 29, 2021

(87) PCT Pub. No.: WO2020/241846
PCT Pub. Date: Dec. 3, 2020

(65) Prior Publication Data
US 2022/0226202 A1    Jul. 21, 2022

(30) Foreign Application Priority Data
May 31, 2019   (JP) ................. 2019-103335

(51) Int. Cl.
*A61K 8/02*     (2006.01)
*A61K 8/81*     (2006.01)
*A61K 8/891*    (2006.01)
*A61Q 19/00*    (2006.01)

(52) U.S. Cl.
CPC ............ *A61K 8/027* (2013.01); *A61K 8/8147* (2013.01); *A61K 8/891* (2013.01); *A61Q 19/00* (2013.01); *A61K 2800/10* (2013.01); *A61K 2800/95* (2013.01)

(58) Field of Classification Search
CPC ...... A61K 8/027; A61K 8/8147; A61K 8/891; A61K 2800/10; A61K 2800/95; A61Q 19/00

See application file for complete search history.

(56) References Cited

U.S. PATENT DOCUMENTS

| | | |
|---|---|---|
| 2002/0098217 A1 | 7/2002 | Piot et al. |
| 2002/0142014 A1 | 10/2002 | Afriat et al. |
| 2002/0182238 A1 | 12/2002 | Creton |
| 2003/0086951 A9 | 5/2003 | Piot et al. |
| 2006/0057085 A1* | 3/2006 | Lezer ............ A61K 8/29 424/63 |
| 2016/0324919 A1* | 11/2016 | Coulter ......... A61K 45/06 |
| 2019/0343731 A1 | 11/2019 | Amari et al. |
| 2020/0030222 A1 | 1/2020 | Hirano et al. |
| 2021/0228457 A1 | 7/2021 | Ishida et al. |

FOREIGN PATENT DOCUMENTS

| | | | |
|---|---|---|---|
| CN | 1350838 A | 5/2002 | |
| CN | 110536673 A | 12/2019 | |
| EP | 903 886 A1 | 11/2021 | |
| JP | 7-196440 A | 8/1995 | |
| JP | 2001-64153 A | 3/2001 | |
| JP | 2001064153 A * | 3/2001 | ............ A61K 8/00 |
| JP | 2002-193746 A | 7/2002 | |
| JP | 2002-293718 A | 10/2002 | |
| JP | 2004-107236 A | 4/2004 | |
| JP | 2007-51106 A | 3/2007 | |
| JP | 2013-6810 A | 1/2013 | |
| JP | 2015-209393 A | 11/2015 | |
| JP | 2016-65030 A | 4/2016 | |
| JP | 2017-109946 A | 6/2017 | |
| JP | 2018-108991 A | 7/2018 | |
| JP | 2018-177804 A | 11/2018 | |
| WO | WO 2014/088072 A1 | 6/2014 | |
| WO | WO 2018/194129 A1 | 10/2018 | |
| WO | WO 2018/194130 A1 | 10/2018 | |

OTHER PUBLICATIONS

International Search Report mailed on Aug. 4, 2020 in PCT/JP2020/021416 filed on May 29, 2020 (2 pages).
Souza et al., "Controlled Release of Linalool Using Nanofibrous Membranes of Poly(lactic acid) Obtained by Electrospinning and Solution Blow Spinning: A Comparative Study", Journal of Nanoscience and Nanotechnology, vol. 15, No. 8, 2015, pp. 5628-5636.
Yu, Shi, "Oji Paper and Nikko Chemicals collaborate to develop cellulose nanofibers for cosmetic applications", China Paper Newsletters, 2013, (with partial unedited computer-generated English translation), 2 pages.
Extended European Search Report issued Jun. 21, 2023 in European Patent Application No. 20815283.5, 4 pages.

* cited by examiner

*Primary Examiner* — Blessing M Fubara
(74) *Attorney, Agent, or Firm* — Oblon, McClelland, Maier & Neustadt, L.L.P.

(57) ABSTRACT

A composition for forming a coating film containing fine fibers, imparting an excellent durability to an obtained coating film. The composition for forming a coating film includes the following components (a) and (b): (a) one or more oil agents selected from the group consisting of ester oil, ether oil, hydrocarbon oil and higher alcohol; and (b) a fiber, at 0.5 mass % or more and 10 mass % or less based on the total composition for forming a coating film, the fiber having an average fiber diameter of 0.1 μm or more and 7 μm or less. The relationship [(average fiber diameter)$^2$/(fiber content)](μm$^2$/mass %) in the composition is 0.005 or more and 7 or less, and the mass ratio of the component (b) to the component (a), (b/a), is 0.005 or more and 5 or less.

20 Claims, 2 Drawing Sheets

COMPOSITION FOR FORMING COATING FILM

FIELD OF THE INVENTION

The present invention relates to a composition capable of forming a coating film containing fine fibers on a surface of a skin.

BACKGROUND OF THE INVENTION

Techniques for incorporating fibers into cosmetics are well known and widely used in mascara and the like. To makeup a keratinous substance such as skin, a composition containing a fiber and a copolymer including a carboxylate group and a polydimethylsiloxane group in a physiologically acceptable medium has been reported (Patent Literature 1). In addition, to reduce the irritation from cosmetics containing irritating components, a technique of incorporating fibers into cosmetics has also been reported. Further, to improve cosmetic durability, a skin cosmetic in which short fibers having a length of 0.1 to 5 mm are formulated has also been reported (Patent Literature 3).

(Patent Literature 1) JP-A-2002-193746
(Patent Literature 2) JP-A-2002-293718
(Patent Literature 3) JP-A-hei 7-196440

The present invention relates to a composition for forming a coating film. The composition comprises the following components (a) and (b):
(a) one or more oil agents selected from the group consisting of an ester oil, an ether oil, a hydrocarbon oil and a higher alcohol; and
(b) a fiber, at 0.5 mass % or more and 10 mass % or less based on the total composition for forming a coating film, having an average fiber diameter of 0.1 μm or more and 7 μm or less.

In the present invention, [(average fiber diameter)$^2$/(fiber content)] (μm$^2$/mass %) is preferably 0.005 or more and 7 or less.

In the present invention, a mass ratio of the component (b) to the component (a), (b/a), is preferably 0.005 or more and 5 or less.

The present invention further relates to a method for producing a coating film on a surface of a skin, the method comprising applying the above composition for forming a coating film to the skin.

The other features of the present invention will be clarified by the claims and the following explanations.

DETAILED DESCRIPTION OF THE INVENTION

Figure 1:
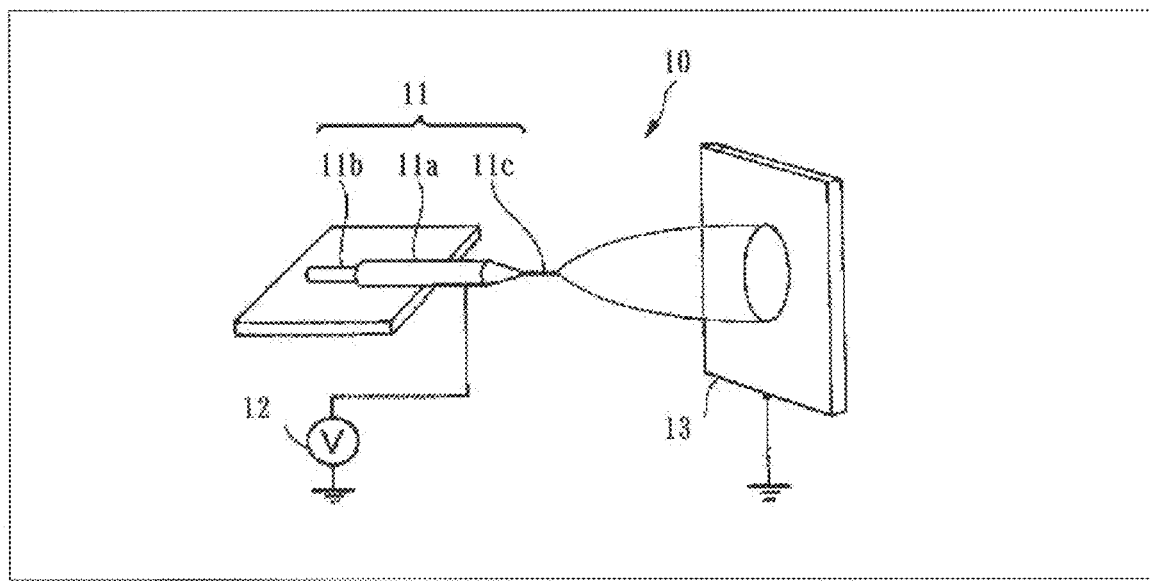
FIG. 1 is a schematic view illustrating the configuration of the electrostatic spraying device used for forming the fibers of the component (b).

The fiber diameter used in Patent Literatures 1 and 2 is as large as 0.9 dtex (=10.7 μm), and the content of fibers is low, and so a fiber network is not formed, and there is an issue in the durability of a cosmetic film. The skin cosmetic composition described in Patent Literature 3 contains a low amount of fibers, thereby the fiber network is not formed, and there is an issue in durability of the obtained cosmetic film.

Accordingly, the present invention relates to provision of a composition capable of forming a coating film having excellent durability.

Use of the composition for forming a coating film of the present invention facilitates to form a coating film having high durability.

The composition for forming a coating film of the present invention comprises the following components (a) and (b):
(a) one or more oil agents selected from the group consisting of an ester oil, an ether oil, a hydrocarbon oil and a higher alcohol; and
(b) a fiber having an average fiber diameter of 0.1 μm or more and 7 μm or less.

The component (a) serves as a dispersion medium for the fiber as the component (b) in the composition of the present invention, and forms a network of the component (b) in the formed coating film to contribute to the durability, more preferably the transparency of the formed coating film.

The component (a) is one or more oil agents selected from the group consisting of an ester oil, an ether oil, a hydrocarbon oil and a higher alcohol, and it is preferable to use two or more oil agents in combination.

Examples of the ester oil include one or more selected from the group consisting of esters of a linear or branched fatty acid and a linear or branched alcohol or a polyhydric alcohol, or triglycerin fatty acid esters (triglyceride).

Specifically, one or more selected from the group consisting of isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di(2-etylhexanoate), dipentaerythritol fatty acid ester, N-alkyl glycol monoisostearate, neopentyl glycol dicaprate, diisostearyl malate, glycerin di(2-heptylundecanoate), trimethylolpropane tri(2-ethylhexanoate), trimethylolpropane triisostearate, pentaerythritol tetra(2-ethylhexanoate), glyceryl tri(2-ethylhexanoate), trimethylolpropane triisostearate, cetyl 2-ethylhexanoate, 2-ethylhexylpalmitate, diethylhexyl naphthalenedicarboxylate, alkyl benzoate (having 12 to 15 carbon atoms), cetearyl isononanoate, glycerin tri(caprylate/caprate), butylene glycol (dicaprylate/caprate), glyceryl trilaurate, glyceryl trimyristate, glyceryl tripalmitate, glyceryl triisostearate, glyceryl tri(2-heptylundecanoate), glyceryl tribehenate, tri-coconut oil fatty acid glyceryl, castor oil fatty acid methyl ester, oleyl oleate, 2-heptylundecyl palmitate, diisobutyl adipate, N-lauroyl-L-glutamic acid-2-octyldodecyl ester, di(2-heptylundecyl) adipate, ethyl laurate, di(2-ethylhexyl) sebacate, 2-hexyldecyl myristate, 2-hexyldecyl palmitate, 2-hexyldecyl adipate, diisopropyl sebacate, di(2-ethylhexyl)succinate, triethyl citrate, 2-ethylhexyl paramethoxycinnamate, and tripropylene glycol dipivalate can be used.

Among these, from the viewpoint of the durability of the formed coating film, at least one selected from the group consisting of octyldodecyl myristate, myristyl myristate, isocetyl stearate, isocetyl isostearate, cetearyl isononanoate, diisobutyl adipate, di(2-ethylhexyl)sebacate, isopropyl myristate, isopropyl palmitate, diisostearyl malate, neopentyl glycol dicaprate, alkyl benzoate (having 12 to 15 carbon atoms) and glycerin tri(caprylate/caprate) is preferable, at least one selected from the group consisting of isopropyl myristate, isopropyl palmitate, diisostearyl malate, neopentyl glycol dicaprate, alkyl benzoate (having 12 to 15 carbon atoms) and glycerin tri(caprylate/caprate) is more preferable, and one or more selected from the group consisting of neopentyl glycol dicaprate, alkyl benzoate (having 12 to 15 carbon atoms), glycerin tri(caprylate/caprate), and isopropyl myristate are even more preferable.

It is even more preferable to use neopentyl glycol dicaprate as the ester oil.

The oil agent in the present invention has an HLB value of 10 or lower, preferably 8 or lower. The HLB value is an index of hydrophilic-lipophilic balance. The present invention employs a value calculated by the following expression from Oda and Teramura et al.

$$HLB = \left(\sum \text{inorganic value} / \sum \text{organic value}\right) \times 10$$

Examples of the ether oil include alkyl-1,3-dimethyl butyl ethers such as cetyl dimethyl butyl ether, ethylene glycol dioctyl ether, glycerol monooleyl ether and dicaprylyl ether, and one or more selected from the group consisting of these ether oils can be used.

It is even more preferable to use cetyl-1,3-dimethyl butyl ether as the ether oil.

Examples of the hydrocarbon oil include hydrocarbon oils which are liquid at 20° C., such as liquid paraffin, squalane, squalene, n-octane, n-heptane, cyclohexane, light isoparaffin and liquid isoparaffin; and hydrocarbon oils which are solid or semisolid at 20° C., such as vaseline, ceresin, paraffin wax, microcrystalline wax, ozokerite, hydrogenated polyisobutene, polyethylene wax and polyolefin wax. One or more selected from the group consisting of liquid paraffin, liquid isoparaffin, squalane, ceresin, paraffin wax, microcrystalline wax, polyethylene wax, polyolefin wax and vaseline are preferable from the viewpoint of the durability of the formed coating film.

The hydrocarbon oil as the component (a) is preferably one that is liquid, solid or semisolid at 20° C., and an oil agent which is hardly volatilized is preferable. In other words, an oil agent which is not volatile is preferable. The oil agent which is hardly volatilized is an oil agent having a property of being hardly volatilized at 25° C. at atmospheric pressure. Preferably, the boiling point at atmospheric pressure is 260° C. or higher, and/or the vapor pressure at 25° C. is preferably 0.02 mmHg or less, more preferably 0.01 mmHg or less. The vapor pressure is preferably lower than that of water.

It is even more preferable to use polyolefin wax, polyethylene wax, paraffin wax, ceresin, microcrystalline wax or vaseline as the hydrocarbon oil.

Examples of the higher alcohol include higher alcohols having 12 to 20 carbon atoms. Specific examples thereof include cetyl alcohol, stearyl alcohol, isostearyl alcohol and oleyl alcohol, and one or more selected from the group consisting of these higher alcohols can be used.

Animal or vegetable oil including the ester oil and hydrocarbon oil can be used. Examples of the animal or vegetable oil include olive oil, jojoba oil, macadamia nut oil, meadowfoam oil, castor oil, safflower oil, sunflower oil, avocado oil, canola oil, apricot kernel oil, rice germ oil and rice bran oil.

It is even more preferable to use olive oil as the animal or vegetable oil.

From the viewpoint of the dispersibility of the component (b) and the durability of the formed coating film and in view of the practical formulation amount, the content of the component (a) in the inventive composition is preferably 0.5 mass % or more, more preferably 1 mass % or more, even more preferably 3 mass % or more.

In view of the practical formulation amount, the content of the component (a) is preferably 99 mass % or less, more preferably 95 mass % or less, even more preferably 90 mass % or less.

The content and the backbone structure of the component (a) can be identified by determining a molecular structure using a known technique such as an NMR (nuclear magnetic resonance apparatus), chromatography or IR analysis, or a combination thereof. By the above-described measurement means, the content of the component (a) can be measured from, for example, the intensity of a measured value at a part showing the backbone structure described above.

The component (b) is a fiber having an average fiber diameter of 0.1 μm or more and 7 μm or less. The component (b) forms a network in the formed coating film to impart the durability to the film. It can be determined whether the fiber forms the network in the formed coating film by a scanning electron microscope (SEM). The network is a state in which fibers dispersed in the coating film have intersections with one another to provide gaps between the fibers, where components contained in the composition for forming a coating film can be held in the gaps. The intersection of the fibers is preferably in a state in which, for example, one fiber has two or more intersections with other two or more fibers, and the fibers are associated with one another.

The average fiber diameter is the diameter of a cross-section of a fiber in principle. Here, when the cross-section of the fiber is circular, the fiber diameter is the diameter of the circle, and when the cross-section of the fiber is elliptic, the fiber diameter is the major axis. The average fiber diameter of the fiber for use in the present invention is 0.1 μm or more and 7 μm or less from the viewpoint of improving the followability of fibers to the skin in the formed coating film, leading to improvement of the durability.

From the viewpoint of improving the durability, the average fiber diameter is preferably 0.2 μm or more, more preferably 0.3 μm or more.

From the viewpoint of improving the durability, the average fiber diameter is preferably 5 μm or less, more preferably 4 μm or less, even more preferably 3 μm or less.

The average fiber diameter can be measured by observing fibers at a magnification of 2 000 times or 5 000 times with SEM, randomly selecting 100 fibers with the exclusion of defects (e.g. lumps of fibers and intersection portions of fibers) among the two-dimensional images of the observed fibers, drawing a line orthogonal to the longer direction of the fiber, and directly reading the fiber diameter. An arithmetic average of these measured values is determined, and defined as the average fiber diameter. Since the fibers are dispersed in the composition for forming a coating film, the composition is thinly applied to a substrate, and measurement is performed by SEM observation.

The length of the fiber is preferably 20 μm or more and 300 μm or less in terms of the average fiber length from the viewpoint of allowing the network to be easily formed, and improving the durability of the formed coating film by the network.

From the viewpoint of easily forming the network, the average fiber length is more preferably 25 μm or more, further more preferably 30 μm or more, even more preferably 40 μm or more.

From the viewpoint of suppressing entanglement and twisting of fibers during application of the composition, the average fiber length is more preferably 250 μm or less, even more preferably 200 μm or less.

The average fiber length can be measured by observing fibers at a magnification of from 250 times to 750 times by SEM, randomly selecting 100 fibers with the exclusion of defects (e.g. lumps of fibers and intersection portions of fibers) among the two-dimensional images of the observed fibers, drawing a line orthogonal to the longer direction of the fiber, and directly reading the fiber length. An arithmetic average of these measured values is determined, and defined as the average fiber length.

The aspect ratio (average fiber length/average fiber diameter) of the fiber is preferably 8 or more and 300 or less from the viewpoint of the durability of the coating film by formation of a uniform network.

From the viewpoint of the durability of the coating film, the aspect ratio is more preferably 10 or more, further more preferably 15 or more, even more preferably 20 or more.

From the viewpoint of the durability of the coating film, the aspect ratio is more preferably 250 or less, even more preferably 200 or less.

The CV value (coefficient of variation) of the average fiber length of the fiber as the component (b) is preferably 40% or more and 100% or less from the viewpoint of formation of the network by the fiber in the coating film.

From the viewpoint of easily forming the network, the CV value is more preferably 42% or more, even more preferably 45% or more.

From the viewpoint of enhancing the storage stability of the composition, the CV value is preferably 95% or less, even more preferably 90% or less.

The CV value may be determined by calculating (standard deviation of measured fiber lengths)/(average fiber length)× 100 [%] from the measured value obtained by the method for measurement of the fiber length.

For the (b) fiber, the proportion of the number of fibers having a fiber length of 40 μm or more in all fibers is preferably 5% or more and 100% or less from the viewpoint of forming a strong network in the coating film to enhance the durability of the resulting coating film.

The fibers having a fiber length of 40 μm or more are contained preferably at 8% or more and 100% or less, and more preferably at 15% or more and 100% or less from the viewpoint of further improving the durability.

The proportion of the number of the fibers may be measured for a total of 200 fibers, where the SEM magnification is adjusted to from 200 times to 750 times depending on the fiber length so that one SEM-photographed image includes from 20 to 30 fibers, and in this state, all fibers present within the image are measured to eliminate arbitrariness.

The (b) fiber, i.e., a fiber of a water-insoluble polymer, can be produced by shortening fibers obtained from a fiber-forming polymer by various known spinning techniques. Here, the fiber-forming polymer is normally a thermoplastic or solvent-soluble chain polymer. A thermoplastic resin is preferable, and a thermoplastic resin having a weight average molecular weight of from $1.0 \times 10^4$ g/mol to $2.0 \times 10^5$ g/mol is more preferable.

Use of water-insoluble polymers, among the fiber-forming polymers, is preferable from the viewpoint of maintaining the shape of fibers in the film-forming agent. The spinning method is preferably an electrospinning method (electrolytic spinning method) from the viewpoint of efficiently obtaining fibers having a small fiber diameter.

The fiber of a water-insoluble polymer refers to one having a property such that in an environment at 1 atm and 23° C., 1 g of the fiber immersed in 10 g of deionized water, and more than 0.5 g of the immersed fiber is undissolved after elapse of 24 hours.

Examples of the water-insoluble polymer include fully saponified polyvinyl alcohols which can be subjected to insoluble treatment after coating film formation, partially saponified polyvinyl alcohols which can be subjected to crosslinking treatment after coating film formation when used in combination with a crosslinker, oxazoline-modified silicones such as poly(N-propanoylethyleneimine)graft-dimethylsiloxane/γ-aminopropylmethylsiloxane copolymers, biodegradable resins such as polyvinyl acetal diethylaminoacetate, Zein (main component of corn protein), polylactic acid (PLA), polybutylene succinate, polyglycolic acid, polycaprolactone and polyhydroxyalkanoic acid, polyester resins such as polyethylene terephthalate (PET) and polybutylene terephthalate, acrylic resins such as polyacrylonitrile resins and polymethacrylic acid resins, polystyrene resins, polyvinyl butyral resins, polyvinyl acetal resins, polyurethane resins, polyamide resins, polyimide resins, polyamideimide resins, polypropylene resins, polyethylene resins, and various polypeptides (e.g. collagen, gelatin, fibrin and casein). These water-insoluble polymers can be used alone, or in combination of two or more thereof.

Among these water-insoluble polymers, one or more selected from the group consisting of fully saponified polyvinyl alcohols which can be subjected to insoluble treatment after coating film formation, partially saponified polyvinyl alcohols which can be subjected to crosslinking treatment after coating film formation when used in combination with a crosslinker, polymethacrylic acid resins and other acrylic resins, polyvinyl butyral resins, polyurethane resins, polylactic acid (PLA), oxazoline-modified silicones such as poly(N-propanoylethyleneimine)graft-dimethylsiloxane/γ-aminopropylmethylsiloxane copolymers, polyvinyl acetal diethylaminoacetate and Zein are preferably used.

Of these, one or more selected from the group consisting of polyvinyl butyral resins, acrylic resins, polypropylene resins, polyester such as polylactic acid, and polyurethane resins are preferable from the viewpoint of ease of formation of nanofibers.

The acrylic resin is preferably an (octylacrylamide/hydroxypropyl acrylate/butylaminoethyl methacrylate) copolymer.

It is also preferable to use a biodegradable resin such as polylactic acid, polybutylene succinate, polyglycolic acid, polycaprolactone or polyhydroxyalkanoic acid from the viewpoint of reducing loads on the environment. The "biodegradability" herein means that the degree of biodegradation of polyester measured in accordance with JIS K6953-1 is 30% or more.

Examples of the fiber shortening treatment means include methods of cutting, shearing, fragmentation, pulverization, crushing or defibration, and for example, mechanical vortex pulverizers, impact pulverizers such as hammer pulverizers, jet pulverizers such as jet mills, media pulverizers such as ball mills and rod mills, cutter mill pulverizers, dry pulverizers such as disc mill pulverizers, media pulverizers using a liquid medium, wet pulverizers using a medialess pulverizer, and combinations thereof can be used. As more preferred means for shortening fibers, a fiber assembly in which nanofibers are interlaced, e.g. a nonwoven fabric, is produced, and the fiber assembly is cut to an appropriate size, followed by using a mechanical vortex pulverizer, a cutter mill pulverizer, a disc mill pulverizer, a wet high-speed shearing medialess pulverizer or a wet high-pressure shearing medialess pulverizer. The fiber assembly includes not only nonwoven fabrics but also fiber assemblies having a predetermined thickness, such as cotton-like materials.

The content of the component (b) in the inventive composition is 0.5 mass % or more and 10 mass % or less based on the total composition for forming a coating film from the viewpoint of the durability of the formed coating film and ease of formation of the fiber network.

From the viewpoint of the durability of the coating film and ease of formation of the fiber network, the content is preferably 0.7 mass % or more, more preferably 1 mass % or more.

From the viewpoint of formability of a stable composition, the content is preferably 9 mass % or less, more preferably 8 mass % or less.

For the content of the component (b) in the total composition for forming a coating film, first, of the fibers contained in the composition, fibers recognized as fibers of a water-insoluble polymer on the basis of the definition of a water-insoluble polymer are obtained. Subsequently, the fibers are washed with a solvent in which the fibers are insoluble, followed by filtering the fibers to obtain only fibers of the water-insoluble polymer. The solvent is preferably ethanol when the resin contained in the component (b) is an ester-based resin such as PLA, and the solvent is preferably water when the resin is an acryl-based resin. The mass can be determined by measuring the fibers of the resulting water-insoluble polymer, and from the ratio of the determined mass to the mass of the composition before washing, i.e. the total composition for forming a coating film, i.e. (mass of component (b) after washing)/(mass of composition before washing)×100 (%).

The mass ratio of the component (b) to the component (a), (b/a), in the inventive composition is 0.005 or more and 5 or less from the viewpoint of the durability of the formed coating film.

The mass ratio (b/a) is preferably 0.02 or more, more preferably 0.05 or more, even more preferably 0.1 or more, from the viewpoint of suppressing stickiness of the composition.

The mass ratio (b/a) is preferably 4 or less from the viewpoint of ease of application of the composition, and is more preferably 3 or less, even more preferably 2 or less, from the viewpoint of improving the appearance.

In the composition of the present invention, the [(average fiber diameter)$^2$/(fiber content)] ($\mu m^2$/mass %) is preferably in the range of 0.005 or more and 7 or less for ensuring that fibers form the network in the formed coating film, and the coating film has good durability.

The fiber content means mass % of fibers in the composition for forming a coating film.

This value is preferably 0.02 or more, more preferably 0.03 or more, even more preferably 0.05 or more, from the viewpoint of sufficiently forming a uniform network of fibers and forming a uniform network of fibers.

In view of the practical formulation amount, this value is preferably 6 or less, more preferably 5 or less, even more preferably 4 or less.

This value, i.e., [(average fiber diameter)$^2$/(fiber content)] ($\mu m^2$/mass %), is an index of the cumulative length of fibers contained in the composition, and the cumulative length decreases as this numerical value increases.

The inventive composition may further contain an oil agent other than the component (a), a volatile component, a surfactant, a polyol which is liquid at 20° C., a preservative, various powders, a moisturizing agent, an ultraviolet absorber, a water-soluble polymer, an amino acid, a pigment and the like.

Examples of the oil agent other than the component (a) include silicone oil and fluorine oil because stickiness can be prevented to exhibit a smooth use impression. Of these, one or more oil agents selected from the group consisting of silicone oil and fluorine oil are contained preferably. However, the content of each of silicone oil and fluorine oil is preferably 80 mass % or less (0 mass % or more and 80 mass % or less), more preferably 0 mass % or more and 75 mass % or less, based on the content of the component (a).

Examples of the silicone oil include dimethylpolysiloxane, polyether-modified silicone, amino-modified silicone, carboxy-modified silicone, methylphenylpolysiloxane, fatty acid-modified silicone, alcohol-modified silicone, fatty alcohol-modified silicone, epoxy-modified silicone, fluorine-modified silicone, cyclic silicone and alkyl-modified silicone.

Examples of the fluorine oil include perfluorodecalin, perfluoroadamantane, perfluorobutyltetrahydrofuran, perfluorooctane, perfluorononane, perfluoropentane, perfluorodecane, perfluorododecane and perfluoropolyether.

The content and the backbone structure of each of silicone oil and fluorine oil can be determined in the same manner as in the case of the component (a).

Examples of the volatile component include water, alcohol, amides, ketone and volatile silicone oil, and one or more selected from the group consisting of water, alcohol and volatile silicone oil are preferable.

As the alcohol, for example, a monohydric chain fatty alcohol, a monohydric cyclic fatty alcohol, or a monohydric aromatic alcohol is suitably used. Examples of the monohydric chain fatty alcohol include $C_1$-$C_6$ alcohols, examples of the monohydric cyclic alcohol include $C_4$-$C_6$ cyclic alcohols, and examples of the monohydric aromatic alcohol include benzyl alcohol and phenylethyl alcohol. Specific examples thereof include ethanol, isopropyl alcohol, butyl alcohol, phenylethyl alcohol, n-propanol and n-pentanol. Ethanol is even more preferable from the viewpoint of safety. One or more selected from the group consisting of these alcohols can be used.

Examples of the volatile silicone oil include dimethylpolysiloxane and cyclic silicone.

Examples of the surfactant include nonionic surfactants, anionic surfactants and cationic surfactants, and examples thereof include polyoxyethylene-methylpolysiloxane copolymers, poly(oxyethylene-oxypropylene)methylpolysiloxane copolymers, crosslinked polyether-modified silicone, crosslinked alkyl polyether-modified silicone, cetyl dimethicone copolyol, propylene glycol monostearate, sorbitan monooleate, glyceryl stearate, polyoxyethylene hydrogenated castor oil, polyoxyethylene alkyl ethers, sorbitan sesquioleate and diglyceryl monooleate. One of these surfactants may be used, or two or more thereof may be used in combination.

Examples of the polyol which is liquid at 20° C. include alkylene glycols such as ethylene glycol, propylene glycol, 1,3-propanediol and 1,3-butanediol; polyalkylene glycols such as diethylene glycol, dipropylene glycol, polyethylene glycol having a weight average molecular weight of 2 000 g/mol or less, and polypropylene glycol; and glycerins such glycerin, diglycerin and triglycerin. Of these, ethylene glycol, propylene glycol, 1,3-butanediol, dipropylene glycol, polyethylene glycol having a weight average molecular weight of 2 000 g/mol or less, glycerin and diglycerin are preferable, propylene glycol, 1,3-butanediol and glycerin are more preferable, and propylene glycol and 1,3-butanediol are even more preferable.

Examples of the preservative include phenoxyethanol, methyl paraoxybenzoate, ethyl paraaminobenzoate, isobutyl paraoxybenzoate, isopropyl paraoxybenzoate, ethyl paraoxybenzoate, butyl paraoxybenzoate, propyl paraoxybenzoate, benzyl paraoxybenzoate and ethyl hexanediol.

The composition of the present invention can be produced by heating and mixing the above-described components as necessary in accordance with conventional methods.

The composition of the present invention is a composition for forming a coating film, and can form an even coating film on a surface of a skin or another substrate when applied to the skin or the substrate. In this coating film, fibers form a network, and the resulting coating film exhibits excellent durability. More preferably, the resulting coating film also exhibits excellent transparency.

Application of the composition of the present invention to a skin enables to form a coating film excellent in durability on the surface of the skin.

Examples of the means for application of the composition to the skin include application with finger(s), application with a spray, application using a tool such as a roller or a sponge, and application of a stick-shaped solid cosmetic composition.

The coating film formed on the surface of the skin according to the present invention preferably exhibits not only excellent durability but also good transparency.

The thickness of the coating film depends on the amount of coating, and is preferably 0.3 μm or more and 30 μm or less, more preferably 0.5 μm or more and 20 μm or less, in normal use (coating basis weight: 1 mg/cm$^2$ or more and 3 mg/cm$^2$). The thickness is measured with a contact thickness meter (LITEMATIC VL-50A manufactured by Mitutoyo Corporation) on the substrate after the application to the substrate. The substrate to be used here is made of PET.

EXAMPLES

Next, the present invention will be described in more detail by way of Examples.

[Production Example of Component (b)]

Example 1 is shown as a production example of short fibers.

(1) The acrylic resin of Table 1, (an (octylacrylamide/hydroxypropyl acrylate/butylaminoethyl methacrylate) copolymer), was dissolved in ethanol to obtain a solution at 18 mass %. Using this solution, a nanofiber sheet was formed on a surface of a collector by an apparatus for an electrospinning method shown in FIG. 1. Production conditions for the nanofibers are as follows.

Applied voltage: 30 kV
Distance between capillary and collector: 150 mm
Discharged amount of aqueous solution: 12 mL/hour
Environment: 25° C., 30% RH (2) The obtained nanofiber sheet was appropriately cut, a DISPER impeller was then attached to a stirring system (LABOLUTION (registered trademark) manufactured by PRIMIX Corporation), and grinding was performed at a rotation speed of 3 000 rpm for 5 minutes to obtain fibers.

In Examples 2 to 10 and 13 to 16, fibers were produced in the same manner as in Example 1 except for the polymer concentrations, rotation speeds and shearing times shown in Table 1.

Example 11 is shown as a production example of short fibers.

(1) The ester resins (polylactic acid) of Table 2 were dissolved in chloroform and dimethylformamide (weight ratio 80:20) to obtain solutions at 20 mass %. Using these solutions, nanofiber sheets were formed on a surface of a collector by the apparatus for the electrospinning method shown in FIG. 1. Production conditions for the nanofibers are as follows.

Applied voltage: 30 kV
Distance between capillary and collector: 150 mm
Discharge amount of aqueous solution: 12 mL/hour
Environment: 25° C., 30% RH (2) Using a dispersing apparatus (MILDER manufactured by Pacific Machinery & Engineering Co. Ltd), the obtained nanofiber sheets were sheared by eight circulations through a circulation line at 13500 rpm to obtain fibers.

In Example 12, fibers were produced in the same manner as in Example 11 except for the polymer concentrations and the numbers of circulations shown in Table 1.

[Production Example of Compositions]

The obtained component (b) was added, and formulation was performed according to Tables 1 and 2 to obtain compositions.

Tables 1 and 2 show the properties of the obtained compositions.

TABLE 1

| | Component | Example 1 Acrylic resin (*1) | Example 2 Acrylic resin (*1) | Example 3 Acrylic resin (*1) | Example 4 Acrylic resin (*1) | Example 5 Acrylic resin (*1) | Example 6 Acrylic resin (*1) | Example 7 Acrylic resin (*1) |
|---|---|---|---|---|---|---|---|---|
| | Polymer concentration [%] | 18 | 18 | 18 | 18 | 21 | 21 | 18 |
| | Stirring method | DISPER | DISPER | DISPER | DI'SPER | DISPER | DISPER | DISPER |
| | Rotation speed [rpm] | 5000 | 5000 | 5000 | 5000 | 6000 | 6000 | 5000 |
| | Shearing time [min] (with DISPER) | 30 | 30 | 30 | 30 | 8 | 8 | 30 |
| | Number of circulations (with MILDER) | — | — | — | — | — | — | — |
| Fiber (b) | Average fiber diameter [μm] X | 0.5 | 0.5 | 0.5 | 0.5 | 1.0 | 1.0 | 0.5 |
| | Average fiber length [μm] Y | 50 | 50 | 50 | 50 | 50 | 50 | 50 |
| | Aspect ratio Y/X | 100 | 100 | 100 | 100 | 50 | 50 | 100 |
| | [(average fiber diameter)$^2$/ (fiber content)] [μm$^2$/mass %] | 0.063 | 0.063 | 0.031 | 0.031 | 0.250 | 0.250 | 0.125 |
| | Fiber content [mass %] | 4.00 | 4.00 | 8.00 | 8.00 | 4.00 | 4.00 | 2.00 |
| (a) | Neopentyl glycol dicaprate (*3) | 4.00 | 1.00 | 8.00 | 2.00 | 4.00 | 1.00 | 31.00 |
| | Cetyl-1,3-dimethyl butyl ether (*4) | 0.00 | 0.00 | 0.00 | 0.00 | 0.00 | 0.00 | 15.00 |
| | Olive oil (*5) | 0.00 | 0.00 | 0.00 | 0.00 | 0.00 | 0.00 | 12.00 |
| | Polyolefin wax (*6) | 0.00 | 0.00 | 0.00 | 0.00 | 0.00 | 0.00 | 1.80 |
| | Polyethylene wax (*7) | 0.00 | 0.00 | 0.00 | 0.00 | 0.00 | 0.00 | 2.50 |

TABLE 1-continued

|   | Component | Example 1 Acrylic resin (*1) | Example 2 Acrylic resin (*1) | Example 3 Acrylic resin (*1) | Example 4 Acrylic resin (*1) | Example 5 Acrylic resin (*1) | Example 6 Acrylic resin (*1) | Example 7 Acrylic resin (*1) |
|---|---|---|---|---|---|---|---|---|
| P | Paraffin wax (*8) | 0.00 | 0.00 | 0.00 | 0.00 | 0.00 | 0.00 | 6.50 |
|   | Ceresin | 0.00 | 0.00 | 0.00 | 0.00 | 0.00 | 0.00 | 6.00 |
|   | Microcrystailine wax | 0.00 | 0.00 | 0.00 | 0.00 | 0.00 | 0.00 | 6.50 |
|   | Vaseline | 0.00 | 0.00 | 0.00 | 0.00 | 0.00 | 0.00 | 7.00 |
|   | Silicone oil | 0.00 | 0.00 | 0.00 | 0.00 | 0.00 | 0.00 | 0.00 |
|   | Fluorine oil | 0.00 | 0.00 | 0.00 | 0.00 | 0.00 | 0.00 | 0.00 |
|   | Purified water | 91.20 | 94.20 | 83.20 | 89.20 | 91.20 | 94.20 | 4.70 |
|   | Ethanol | 0.00 | 0.00 | 0.00 | 0.00 | 0.00 | 0.00 | 0.00 |
|   | SIMULGEL EG (*9) | 0.30 | 0.30 | 0.30 | 0.30 | 0.30 | 0.30 | 0.00 |
|   | Polyoxyethylene sorbitan monostearate(20E.O.) (*10) | 0.50 | 0.50 | 0.50 | 0.50 | 0.50 | 0.50 | 0.00 |
|   | Polyoxyethylene (10) hydrogenated castor oil (*11) | 0.00 | 0.00 | 0.00 | 0.00 | 0.00 | 0.00 | 1.50 |
|   | Polyoxyethylene (20) hydrogenated castor oil (*12) | 0.00 | 0.00 | 0.00 | 0.00 | 0.00 | 0.00 | 3.50 |
|   | Others (preservative) | 0.00 | 0.00 | 0.00 | 0.00 | 0.00 | 0.00 | 0.00 |
|   | Total | 100.00 | 100.00 | 100.00 | 100.00 | 100.00 | 100.00 | 100.00 |
|   | (a) | 4.00 | 1.00 | 8.00 | 2.00 | 4.00 | 1.00 | 88.30 |
|   | (b)/(a) | 1.00 | 4.00 | 1.00 | 4.00 | 1.00 | 4.00 | 0.02 |
|   | P/((a) + P) [%] | 0.0 | 0.0 | 0.0 | 0.0 | 0.0 | 0.0 | 0.0 |
| Evaluation | Durability | 4 | 3 | 3 | 3 | 3 | 3 | 4 |
|   | Transparency | 4 | 3 | 4 | 3 | 3 | 3 | 4 |
|   | Network formability | formed | formed | formed | formed | formed | formed | formed |

TABLE 2

|   | Component | Example 8 Acrylic resin (*1) | Example 9 Acrylic resin (*1) | Example 10 Acrylic resin (*1) | Example 11 Ester resin (*1) | Example 12 Ester resin (*1) |
|---|---|---|---|---|---|---|
|   | Polymer concentration [%] | 18 | 24 | 27 | 20 | 18 |
|   | Stirring method | DISPER | DISPER | DISPER | MILDER | MILDER |
|   | Rotation speed [rpm] | 5000 | 3500 | 3000 | 13500 | 13500 |
|   | Shearing time [min] (with DISPER) | 30 | 10 | 30 | — | — |
|   | Number of circulations (with MILDER) | — | — | — | 8 | 5 |
| Fiber (b) | Average fiber diameter [μm] X | 0.5 | 2.0 | 4.0 | 0.7 | 0.5 |
|   | Average fiber length [μm] Y | 50 | 50 | 50 | 30 | 30 |
|   | Aspect ratio Y/X | 100 | 25 | 13 | 43 | 60 |
|   | [(average fiber diameter)$^2$/ (fiber content)] [μm$^2$/mass %] | 0.063 | 1.000 | 4.000 | 0.123 | 0.063 |
|   | Fiber content [mass %] | 4.00 | 4.00 | 4.00 | 4.00 | 4.00 |
| (a) | Neopentyl glycol dicaprate (*3) | 6.30 | 17.50 | 17.50 | 17.50 | 15.70 |
|   | Ceresin | 3.50 | 0.00 | 0.00 | 0.00 | 0.70 |
|   | Vaseline | 0.00 | 0.00 | 0.00 | 0.00 | 0.00 |
| P | Silicone oil | 6.30 | 0.00 | 0.00 | 0.00 | 48.00 |
|   | Fluorine oil | 0.00 | 0.00 | 0.00 | 0.00 | 0.00 |
|   | Purified water | 54.37 | 76.35 | 76.35 | 67.35 | 11.69 |
|   | Ethanol | 0.00 | 0.00 | 0.00 | 9.00 | 6.00 |
|   | Glycerin | 16.00 | 0.00 | 0.00 | 0.00 | 7.00 |
|   | 1,3-Butylene glycol | 5.00 | 0.00 | 0.00 | 0.00 | 1.50 |
|   | Polyetheyle glycol | 3.00 | 0.00 | 0.00 | 0.00 | 0.00 |
|   | SIMULGEL EG (*9) | 0.23 | 0.15 | 0.15 | 0.15 | 0.41 |
|   | Polyoxyethylene sorbitan monostearate(20E.O.) (*10) | 0.60 | 1.60 | 1.60 | 1.60 | 5.00 |
|   | Preservative | 0.40 | 0.40 | 0.40 | 0.40 | 0.00 |
|   | pH regulator | 0.30 | 0.00 | 0.00 | 0.00 | 0.00 |
|   | Total | 100.00 | 100.00 | 100.00 | 100.00 | 100.00 |
|   | (a) | 9.80 | 17.50 | 17.50 | 17.50 | 16.40 |
|   | (b)/(a) | 0.41 | 0.23 | 0.23 | 0.23 | 0.24 |
|   | P/((a) + P) [%] | 39.1 | 0.0 | 0.0 | 0.0 | 74.5 |
| Evaluation | Durability | 4 | 4 | 3 | 4 | 4 |
|   | Transparency | 4 | 4 | 4 | 4 | 4 |
|   | Network formability | formed | formed | formed | formed | formed |

*1: AMPHOMER 28-4910 (Akzo Nobel N.V.)
*2: Ingeo6252D (Natureworks)
*3: ESTEMOL N-01 (The Nisshin Oillio Group, Ltd.)
*4: ASE-166K (Kao Corporation)
*5: CROPURE OL-LQ-(JP) (Croda Japan KK)
*6: PERFORMALENE 700EP (NEW PHASE TECHNOLOGIES)
*7: PERFORMALENE 655 (NEW PHASE TECHNOLOGIES)
*8: HNP-9 (NIPPON SEIRO CO., LTD.)
*9: SIMULGEL EG (SEPPIC)

*10: RHEODOL TW-S120V (Kao Corporation)
*11: NIKKOL HCO-10 (Nikko Chemicals Co., Ltd.)
*12: NIKKOL HCO-20 (Nikko Chemicals Co., Ltd.)
*13: PARLEAM 4 (NOF Corporation)
*14: NIKKOL SQUALANE (Nikko Chemicals Co., Ltd.)
*15: SHIRONIBAR 0.5-6D (Cosmeterials KK)
Silicone oil used in Example 8: dimethyl polysiloxane (1.3% of KF-96A-10cs and 5% of KF-96A-50cs manufactured by Shin-Etsu Chemical Co., Ltd.)
Silicone oil used in Example 12: dimethyl polysiloxane (0.7% of KF-96A-2cs, 0.5% of KF-96A-6cs and 21% of KF-96A-10cs manufactured by Shin-Etsu Chemical Co., Ltd.), olyether-modified silicone (25% of SH3775 M manufactured by Dow Toray Co., Ltd. and 0.6% of KF-6015 manufactured by Shin-Etsu Chemical Co., Ltd.) and cyclic silicone (0.2% of TSF405A manufactured by Momentive Performance Materials Japan LLC.)

Examples 1 to 12

The compositions of Tables 1 and 2 were produced, and each uniformly applied to an artificial leather to form a coating film. The properties of the formed coating films were evaluated.

Evaluation Methods (1) Durability

The composition was applied to the artificial leather at 2 mg/cm$^2$, and dried for 15 minutes, the coating film was then scraped maximum 20 times with a finger at a load of from 20 to 50 gf, and whether the fiber was peeled or not was evaluated.
4: Not peeled.
3: Peeled at the tenth scraping.
2: Peeled at the fifth scraping.
1: Peeled at the first scraping.
(2) Transparency To the front arm of each of five men and women in their twenties to thirties, the composition was applied at 2 mg/cm$^2$ and dried for 15 minutes, and the coating film was then visually observed, and evaluated for transparency. In spreading of the composition, the composition was taken by a dominant hand, and applied to the arm of the other hand, and the composition was spread over the arm. A region of 5 cm×5 cm was marked as a portion to which the composition was applied, and 50 mg of the composition was taken by the hand, and uniformly spread. In application of the composition, a site where the arm had no scar and little arm hair was selected. The table shows evaluation results each associated with the largest number of persons among the five persons.
4: The coating film is transparent, so that the boundary with a composition-non-coated portion is obscure.
3: The coating film is generally transparent, and looks white when viewed from some angle.
2: The coating film is only slightly powdery, but is fully recognizable.
1: The coating film is generally powdery, or fibers are visually recognizable.
(3) Network formation It was evaluated by SEM whether a network was formed. In evaluation of network formation, when fibers each had two or more intersections with other fibers and a state in which gaps surrounded by the fibers are present was recognized overall, it was judged that the network was determined to be formed.

Figure 2:
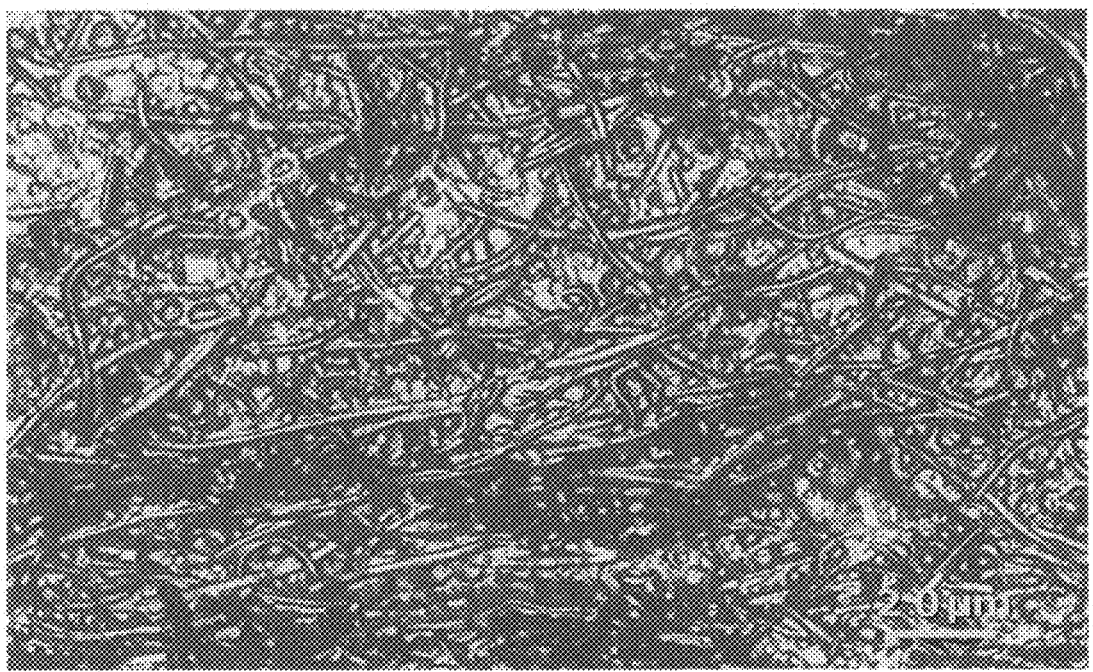
FIG. 2 shows a reference example of an SEM image with network formation.
Figure 3:
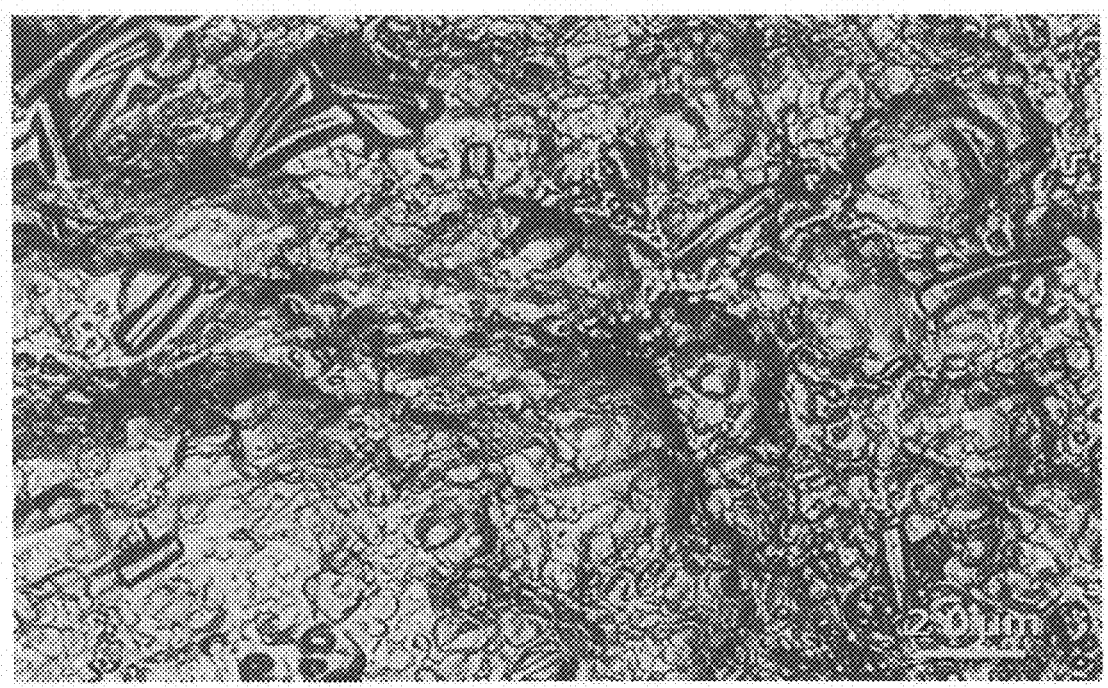
FIG. 3 shows a reference example of an SEM image without network formation.

Tables 1 and 2 show the results. FIG. 2 shows a SEM reference image in which the network is formed and FIG. 3 shows a SEM reference image in which the network is not formed, where on the basis of the images, whether the network was formed or not was determined in Examples and Comparative Examples.

Examples 13 to 16 and Comparative Examples 1 and 2

The compositions of Table 3 were produced, and each uniformly applied to an artificial leather to form a coating film. The properties of the formed coating films were evaluated. The evaluation method is the same as described above. Table 3 shows the results.

TABLE 3

| | Component | Example 13 Acrylic resin (*1) | Example 14 Acrylic resin (*1) | Example 15 Acrylic resin (*1) | Example 16 Acrylic resin (*1) | Comparative Example 1 Nylon (*15) | Comparative Example 2 Acrylic resin (*1) |
|---|---|---|---|---|---|---|---|
| | Polymer concentration [%] | 18 | 18 | 21 | 24 | — | 18 |
| | Stirring method | DISPER | DISPER | DISPER | DI'SPER | — | DISPER |
| | Rotation speed [rpm] | 3500 | 8000 | 6000 | 4000 | — | 10000 |
| | Shearing time [min] (with DISPER) | 15 | 15 | 15 | 15 | — | 90 |
| | Number of circulations (with MILDER) | — | — | — | — | — | — |
| Fiber (b) | Average fiber diameter [μm] X | 0.5 | 0.5 | 1 | 2 | 43 | 0.5 |
| | Average fiber length [μm] Y | 88 | 30 | 30 | 30 | 500 | 9 |
| | Aspect ratio Y/X | 176 | 60 | 30 | 15 | 12 | 18 |
| | [(average fiber diameter)$^2$/ (fiber content)] [μm$^2$/mass %] | 0.063 | 0.063 | 0.250 | 0.667 | 3698.000 | 2.924 |
| | Fiber content [mass %] | 4.00 | 4.00 | 4.00 | 6.00 | 0.50 | 0.90 |
| (a) | Neopentyl glycol dicaprate (*3) | 17.50 | 0.00 | 0.00 | 0.00 | 17.50 | 17.50 |
| | Liquid isoparaffin (*13) | 0.00 | 0.00 | 0.00 | 0.00 | 0.00 | 0.00 |
| | Squalane (*14) | 0.00 | 3.00 | 3.00 | 3.00 | 0.00 | 0.00 |
| | Purified water | 76.35 | 86.85 | 86.85 | 84.85 | 79.50 | 79.91 |

TABLE 3-continued

| Component | | Example 13 Acrylic resin (*1) | Example 14 Acrylic resin (*1) | Example 15 Acrylic resin (*1) | Example 16 Acrylic resin (*1) | Comparative Example 1 Nylon (*15) | Comparative Example 2 Acrylic resin (*1) |
|---|---|---|---|---|---|---|---|
| | SIMULGEL EG (*9) | 0.15 | 0.15 | 0.15 | 0.15 | 0.50 | 0.50 |
| | Polyoxyethylene sorbitan monostearate(20E.O.) (*10) | 1.60 | 1.60 | 1.60 | 1.60 | 1.60 | 1.60 |
| | Preservative | 0.40 | 0.40 | 0.40 | 0.40 | 0.40 | 0.40 |
| | Total | 100.00 | 100.00 | 100.00 | 100.00 | 100.00 | 100.00 |
| | (b)/(a) | 0.23 | 0.57 | 0.57 | 0.86 | 0.03 | 0.00 |
| Evaluation | Durability | 4 | 4 | 4 | 3 | 1 | 2 |
| | Transparency | 4 | 4 | 4 | 4 | 1 | 4 |
| | Network formability | formed | formed | formed | formed | formed | formed |

REFERENCE SIGNS LIST

10 Electrostatic spray apparatus
11 Syringe
12 High-voltage source
13 Conductive collector
11a Cylinder
11b Piston
11c Capillary

The invention claimed is:

1. A composition for forming a coating film, wherein the composition comprises the following components:
   (a) one or more oil agents selected from the group consisting of an ester oil, an ether oil, a hydrocarbon oil, and a higher alcohol;
   (b) a fiber, at 0.5 mass % or more and 10 mass % or less based on the total composition, having an average fiber diameter of 0.1 μm or more and 7 μm or less, and water, at concentration of 11.69 mass % or more based on the total composition, and
   wherein [(average fiber diameter)$^2$/(fiber content)] (μm$^2$/mass %) is 0.005 or more and 7 or less,
   wherein a mass ratio of the component (b) to the component (a), (b/a), is 0.005 or more and 5 or less, and
   wherein the composition is in liquid form.

2. The composition for forming a coating film according to claim 1, further comprising a component (c):
   (c) one or more volatile components selected from the group consisting of ethanol, isopropyl alcohol, butyl alcohol, phenylethyl alcohol, n-propanol, and n-pentanol.

3. The composition for forming a coating film according to claim 2, wherein the component (c) is ethanol.

4. The composition for forming a coating film according to claim 1, wherein an aspect ratio [(average fiber length)/(average fiber diameter)] of the (b) fiber is 8 or more and 200 or less.

5. The composition for forming a coating film according to claim 1, wherein an average fiber length of the (b) fiber is 30 μm or more and 300 μm or less.

6. The composition for forming a coating film according to claim 1, wherein the (b) fiber comprises a thermoplastic resin.

7. The composition for forming a coating film according to claim 1, wherein the (b) fiber is dispersed in the (a) oil agent which serves as a dispersion medium, and the composition is for forming a coating film on a skin.

8. The composition for forming a coating film according to claim 1, wherein the component (a) is one or more oil agents selected from the group consisting of an ester oil, an ether oil, and a hydrocarbon oil which is in a liquid state at 20° C.

9. The composition for forming a coating film according to claim 1, wherein the (a) oil agent has an HLB value of 10 or lower.

10. The composition for forming a coating film according to claim 1, wherein the average fiber diameter of the (b) fiber is 0.2 μm or more and 7 μm or less.

11. The composition for forming a coating film according to claim 1, wherein the component (b) is a fiber of a water-insoluble polymer.

12. The composition for forming a coating film according to claim 1, wherein a content of the component (a) is 0.5 mass % or more and 99 mass % or less relative to a total mass of the composition for forming a coating film.

13. The composition for forming a coating film according to claim 1, wherein a content of the component (b) is 0.5 mass % or more and 8 mass % or less relative to a total mass of the composition for forming a coating film.

14. The composition for forming a coating film according to claim 1, wherein a mass ratio of the component (b) to the component (a), (b/a), is 0.1 or more and 2 or less.

15. The composition for forming a coating film according to claim 1, wherein in the (b) fiber, a proportion of the number of fibers having a fiber length of 40 μm or more in all fibers is 15% or more and 100% or less.

16. A method for producing a coating film on a surface of a skin, the method comprising applying the composition for forming a coating film according to claim 1 to the skin.

17. A coating film comprising the composition for forming a coating film according to claim 1.

18. The composition for forming a coating film according to claim 1, further comprising a component (c):
   (c) one or more volatile components selected from the group consisting of dimethylpolysiloxane and cyclic silicone.

19. The composition for forming a coating film according to claim 1, wherein the (a) one or more oil agents comprises a hydrocarbon oil comprising one or more selected from the group consisting of polyolefin wax, polyethylene wax, paraffin wax, ceresin, microcrystalline wax.

20. The composition for forming a coating film according to claim 1, wherein the (a) one or more oil agents comprises an ester oil comprising one or more selected from the group consisting of neopentyl glycol dicaprate, alkyl benzoate (having 12 to 15 carbon atoms), glycerin tri(caprylate/caprate), and isopropyl myristate.

* * * * *